United States Patent [19]
Chien

[11] Patent Number: 5,497,650
[45] Date of Patent: Mar. 12, 1996

[54] PNEUMATIC GOLF CLUB TESTING APPARATUS

[75] Inventor: Kun-Lin Chien, Nai-Tou, Taiwan

[73] Assignee: Heng-An Co., Ltd., Nai-Tou, Taiwan

[21] Appl. No.: 424,169

[22] Filed: Apr. 19, 1995

[51] Int. Cl.⁶ .................................................... G01N 3/00
[52] U.S. Cl. ........................ 73/12.07; 73/12.11
[58] Field of Search .............................. 273/26 D, 26 A, 273/25; 73/12.7, 12.11

[56] References Cited

U.S. PATENT DOCUMENTS

| | | | |
|---|---|---|---|
| 3,777,548 | 12/1973 | Nicolaides | 73/12.11 |
| 4,074,905 | 2/1978 | High | 273/26 A |
| 4,703,931 | 11/1987 | Steen | 273/26 A |
| 4,774,928 | 10/1988 | Kholin | 273/26 D |
| 5,160,131 | 11/1992 | Leon | 273/26 D |

FOREIGN PATENT DOCUMENTS

| | | | |
|---|---|---|---|
| 2706779 | 12/1994 | France | 273/29 A |

*Primary Examiner*—Richard Chilcot
*Assistant Examiner*—Ronald Biegel
*Attorney, Agent, or Firm*—W. Wayne Liauh

[57] ABSTRACT

A pneumatic golf testing apparatus composes of an air cylinder, an accumulator, a barrel, a ball bucket, a ball cage, a golf head clamps and a frame. Air cylinder pumps compressed air into the accumulator and controls the opening and closing of a valve to allow the pressurized air discharging out of the accumulator and to eject the golf ball out of the barrel at a very high speed. The flying ball hits a golf head held by a golf head clamps disposed on a wall in the ball cage. The golf ball then drops in the ball cage for collection and reuse. The testing can be repetitively performed for testing the structural strength, base binding strength and lacquer density of the golf head. The testing is not destructive and can be done in short period of time without a complete set of a golf club.

5 Claims, 5 Drawing Sheets

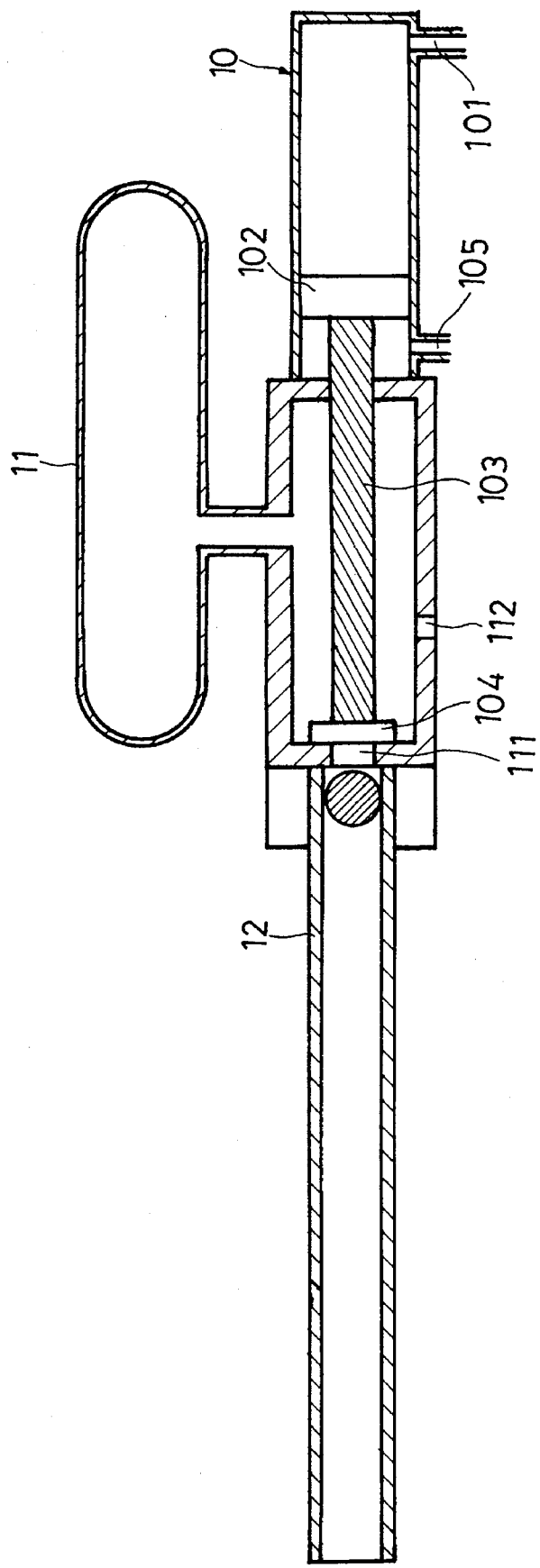
F I G. 3

PNEUMATIC GOLF CLUB TESTING APPARATUS

BACKGROUND OF THE INVENTION

Conventionally golf club factories usually use material testing apparatus or impact testing apparatus to test the structural strength of the head of a golf club. These apparatus commonly use metallic test holders and often cause damage of the testing head. Some factories try to use a robot to actually swing a golf club for testing. This approach requires a complete set of golf clubs. Referring to FIG. 1, a complete golf club consists of a grip (A), a head (B), a neck (C), and a shaft (D). Testing by a robot is a lengthy process and often results in the breaking of the shaft (D).

SUMMARY OF THE INVENTION

The present invention relates to a pneumatic golf testing apparatus which consists of an air cylinder, an accumulator, a barrel, a ball bucket, a ball cage, a head clamp and a frame. The accumulator discharges the compressed air instantly through the control of the air cylinder, causing a ball, which has dropped into the barrel from the ball bucket, to be ejected at very high speed. The ejected ball hits the head of the golf club, which is held by a head clamp, and falls into the ball cage where it can be collected for re-use. The above testing cycle can be performed repeatedly to test the structural strength of the head of golf clubs, as well as their base binding strength and the lacquer coverage density.

The primary object of the present invention is to provide compressed air to drive a golf ball flying at high speed to hit the head face of a golf club. The present invention does not need a complete golf club to do a destructive testing. Furthermore, the head clamp has die plastics as padding which can protect the testing head from damage. The testing can be done in a short period of time. It can also be done by sampling testing at the production line rather than after the completed assembly of the entire club, thus significantly improving the testing efficiency.

BRIEF DESCRIPTION OF THE DRAWINGS

FIG. 3 is a cross-sectional view of an accumulator and an air cylinder of the present invention.

DETAILED DESCRIPTION OF THE EMBODIMENTS

Figure 1:
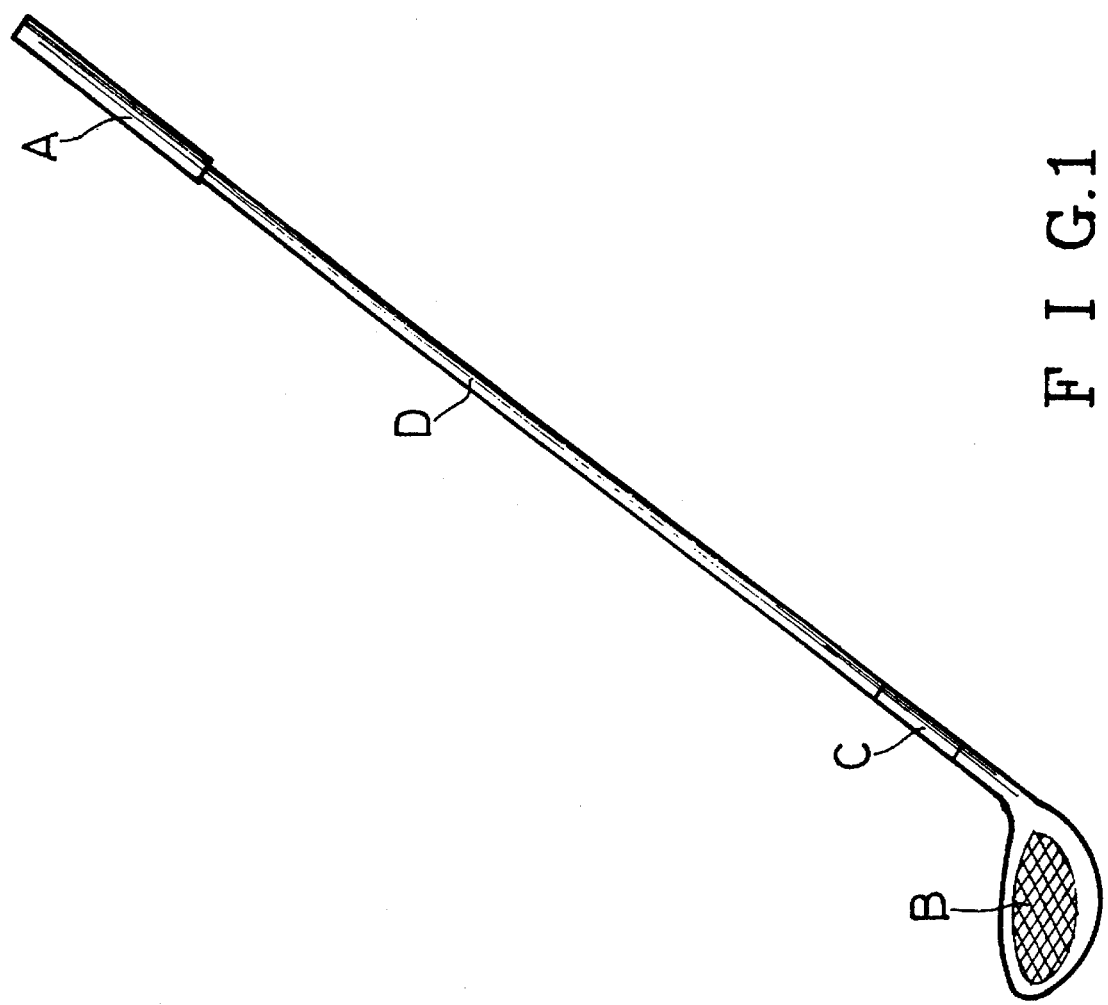
FIG. 1 is a pictorial view of a conventional golf club.
Figure 2:
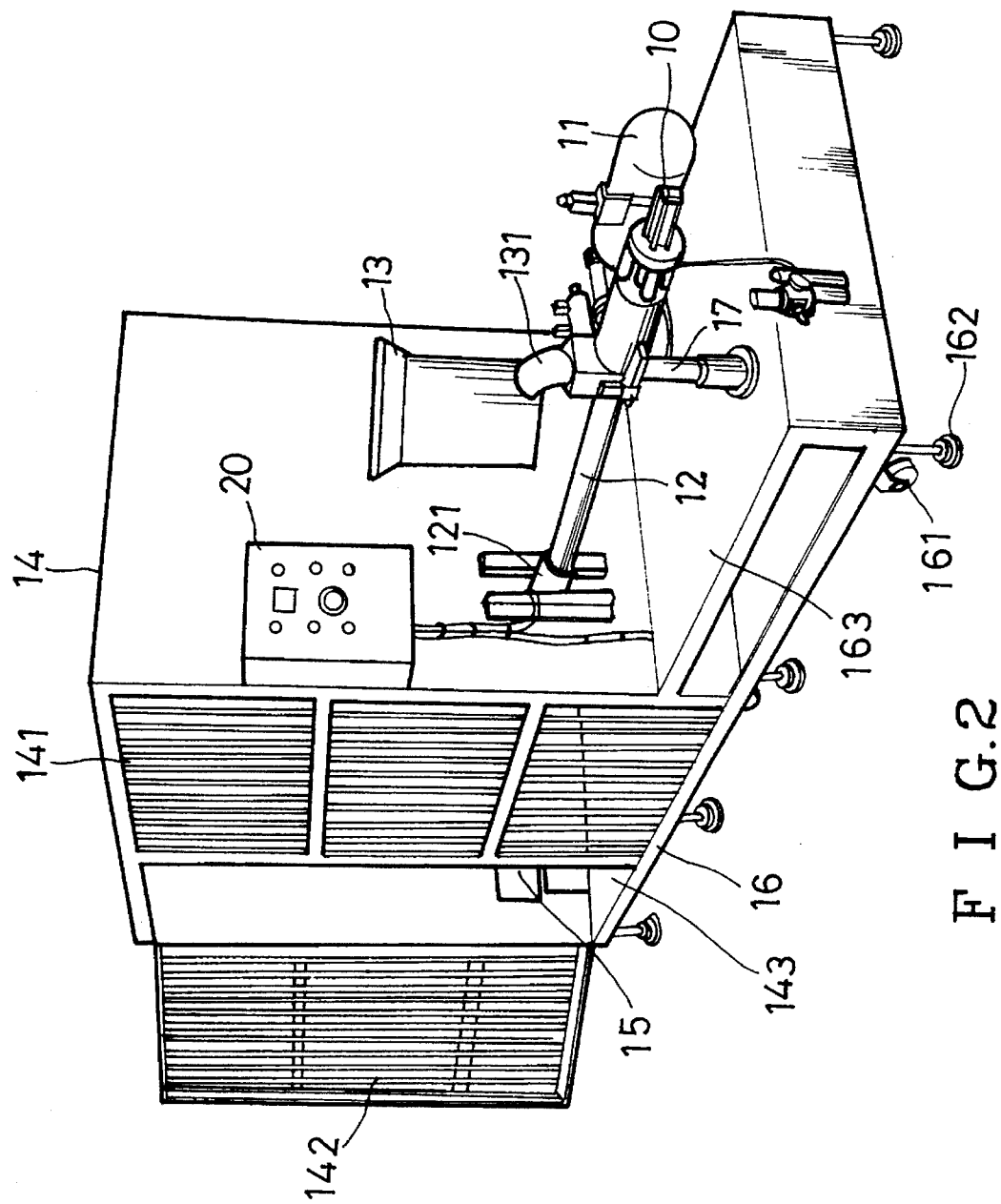
FIG. 2 illustrates a pictorial view of the present invention.

Referring to FIG. 2, the present invention includes an air cylinder (10), an accumulator (11), a barrel (12), a ball bucket (13), a ball cage (14), a head clamp (15) and a frame (16). Under the base frame (16), there are a number of casters (161) and supports (162). Above the frame (16) is a substantially flat platform (163). A pillar (17) is positioned vertically on the platform (163) to support a horizontally positioned air cylinder (10), an accumulator (11) and barrel (12). Accumulator (11) is positioned behind the barrel (12). Through the control of air cylinder (10), the accumulator (11) can discharge the compressed air into barrel (12) instantly. The ball bucket (13) is positioned above the rear end of the barrel (12). A tube (131) allows balls from the ball bucket (B) moving into a ball filling inlet (18) formed between the accumulator (11) and the barrel (12). When a ball is moved into the filling inlet (18), an automatic starter (19) senses the ball and triggers the accumulator (11) to discharge compressed air into barrel (12). The golf ball is ejected from the barrel (12) at high speed (more than 450 km/hour). The flying ball hits the head of a golf club held by a head clamp positioned against a wall of the ball cage (14). A control box (20) with internal circuits is installed outside of a rear wall of the ball cage (14).

Referring to FIG. 3, compressed air enters into the air cylinder (10) through an air intake (101) at the rear end of the air cylinder, and pushes a piston (102) moving forward. Through a piston rod (103), a valve (104) is closed at the exit (111) formed between the accumulator (11) and the barrel (12). The compressed air enters into the accumulator (11) through an air inlet (112) which is closed when the compressed air is exhausted.

After compressed air enters the air cylinder (10) through another air inlet (105) at the front end, the air inlet (101) becomes an air exit, and piston (102) is moved quickly to the rear. The piston rod (103) opens the valve (104). The pressurized air in the accumulator (11) is released and discharged into the barrel (12). A ball dropped on the rear end of barrel (12) is ejected from the barrel by the discharged air at very high speed to hit the testing head.

The ball cage (14) can be in any suitable shape and size, and is positioned at one end of the frame (16) and is connected with one end of the barrel (12). FIG. 2 illustrates an embodiment of a ball cage (14) in a substantially rectangular cubic box. One wall is formed by rails (141) with an interval less than the diameter of a golf ball and has a door (142). The floor (143) of the ball cage (14) is substantially flat and can be slightly inclined toward the rail wall (141) to allow the balls dropping in the cage be moved to the door (142) side for ease of collection. A head clamp (15) is positioned in the cage on a wall opposite to the barrel opening (121) for holding a testing head of the golf club.

Figure 4:
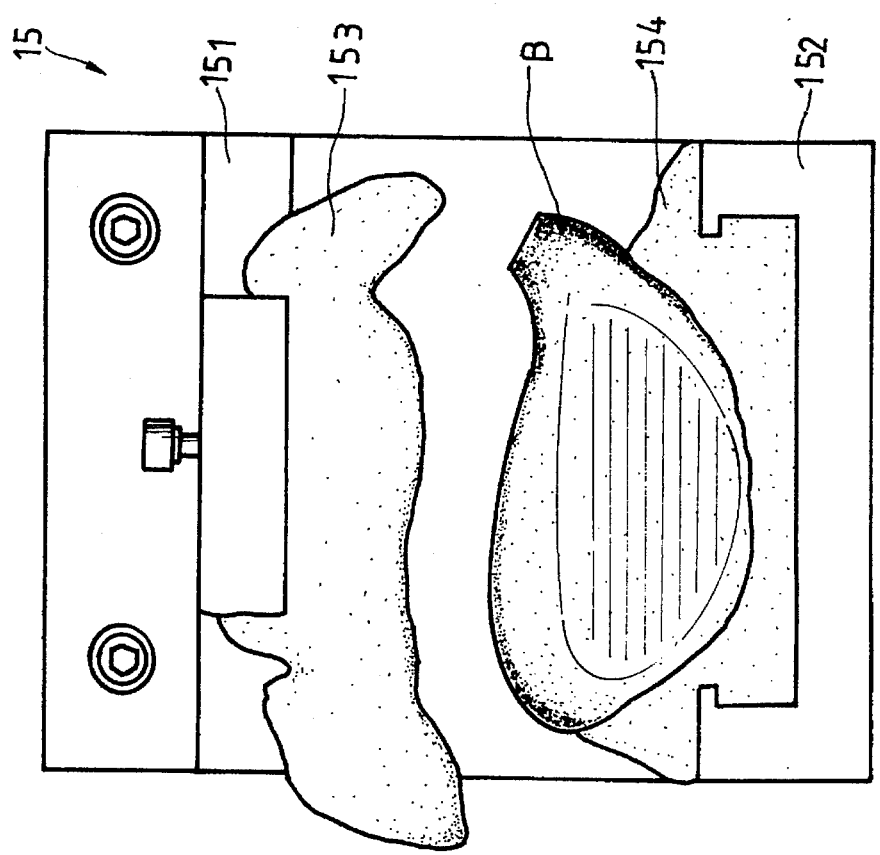
FIG. 4 is a plan view of a head clamp of the present invention.
Figure 5:
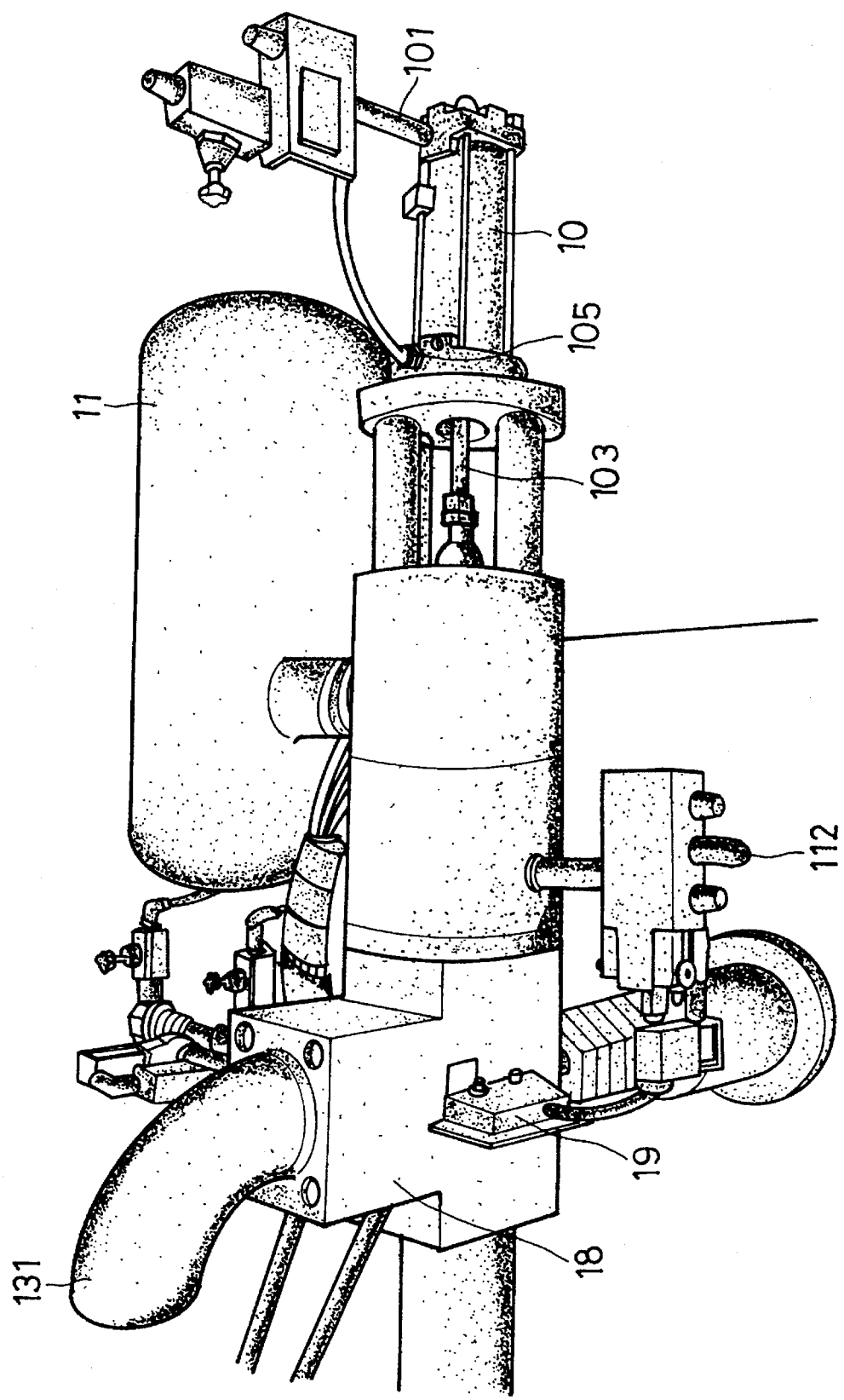
FIG. 5 is a pictorial view of an accumulator and an air cylinder of the present invention.

Referring to FIG. 4, a head clamp (15) includes an upper die holder (151), a lower die holder (152), an upper die (153) and a lower die (154). The upper die holder (151) and lower die holder (152) are made from metallic materials. The upper die (153) and lower die (154) are made from plastics and are positioned on the upper die holder (151) and lower die holder (152) respectively. Dies (153) and (154) can be made by melting the plastics in 100° C. hot water and pouring into dies, then cooling at room temperature to shape into the forms required. The golf head can be clamped by means of an air cylinder which moves the upper or lower die holder. The testing head of the golf club can be positioned in the upper and lower die holders in different manners, either to be surrounded completely or partly, to simulate different testing conditions. This is in contrast to the conventional testing method which requires cutting away the hitting surface of the golf head for holding and testing.

The present invention allows the pressurized air discharged from the accumulator (11) into the barrel (12) and causing the golf ball to fly at very high speed and hit the golf head held by head clamps (15). While the motion is significantly different from the swinging of a golf club it has the same effect. The present invention allows testing without a complete set of a golf clubs. It can be performed repeatedly at the production line in a short time period. It can test at various conditions to get the required testing data without harmful effect to the head of the golf club.

I claim:

1. A pneumatic golf club testing apparatus comprising:

an air cylinder having a piston and a piston rod disposed therein;

an accumulator to contain pressurized air having an air inlet directing toward said air cylinder;

a barrel having one end connecting with an air exit which has a pair of air flow paths directed respectively to said air cylinder and said accumulator;

a ball bucket disposed above said barrel and having a tube connected to a hollow section formed between said accumulator and said barrel;

a ball cage having one wall connecting with an opening end of said barrel and having a rail wall which has an interval less than the diameter of a golf ball, said rail wall having a door, said ball cage further having a head clamp disposed on a wall in opposite side of the opening of said barrel; and a frame disposed at one end of said ball cage and having a pillar disposed thereon to support said barrel, said air cylinder, and said accumulator; whereas said air cylinder can trigger the pressurized air in said accumulator to discharge into said barrel to eject a golf ball dropping from said bull bucket out of said barrel at high speed to bit a golf club head held in said head clamps for testing a structural strength, binding strength and lacquer covering density of the golf club head.

2. A golf club testing apparatus of claim 1 further having an air exit formed between said accumulator and said barrel, said air exit is covered by a valve which can be opened or closed by said piston rod thus to allow the pressurized air to discharge out of said air exit from said accumulator when said valve is open.

3. A golf testing apparatus of claim 1, wherein said head clamp having an upper die holder, a lower die holder, an upper die, and a lower die, said upper die and low die are made from plastics, said air cylinder can move said upper die holder or said lower die holder to make said upper die and said lower die to hold said golf club head.

4. A golf club testing apparatus of claim 1, wherein said ball cage further has an inclined floor to facilitate a collection of golf balls dropped inside said ball cage.

5. A golf club testing apparatus of claim 1 further having an automatic starter to sense the existence of a golf ball dropping from said ball basket into one end of said barrel and to trigger said accumulator for ejecting said golf ball out of said barrel.

* * * * *